US012779070B2

(12) United States Patent
Furukawa et al.

(10) Patent No.: US 12,779,070 B2
(45) Date of Patent: Nov. 3, 2026

(54) ACTIVE OXYGEN SUPPLY DEVICE, DEVICE FOR CONDUCTING TREATMENT BY ACTIVE OXYGEN, AND METHOD FOR CONDUCTING TREATMENT BY ACTIVE OXYGEN

(71) Applicant: CANON KABUSHIKI KAISHA, Tokyo (JP)

(72) Inventors: Takumi Furukawa, Shizuoka (JP); Kazuhiro Yamauchi, Shizuoka (JP); Masaki Ozawa, Shizuoka (JP); Kenji Takashima, Kanagawa (JP); Yuichi Kikuchi, Shizuoka (JP); Shota Kaneko, Tokyo (JP); Masatsugu Hongo, Shizuoka (JP)

(73) Assignee: Canon Kabushiki Kaisha, Tokyo (JP)

( * ) Notice: Subject to any disclaimer, the term of this patent is extended or adjusted under 35 U.S.C. 154(b) by 961 days.

(21) Appl. No.: 18/090,700

(22) Filed: Dec. 29, 2022

(65) Prior Publication Data

US 2023/0146111 A1 May 11, 2023

Related U.S. Application Data

(63) Continuation of application No. PCT/JP2021/024688, filed on Jun. 30, 2021.

(30) Foreign Application Priority Data

Jun. 30, 2020 (JP) ................................ 2020-113518
Oct. 21, 2020 (JP) ................................ 2020-176934
(Continued)

(51) Int. Cl.
*A61L 2/20* (2026.01)
*A61L 2/10* (2006.01)
*A61L 2/202* (2026.01)

(52) U.S. Cl.
CPC ................. *A61L 2/202* (2013.01); *A61L 2/10* (2013.01)

(58) Field of Classification Search
CPC .............. A61L 2/202; A61L 2/10; A61L 2/14; A61L 2103/23; A61L 2103/15; A61L 2/20;
(Continued)

(56) References Cited

U.S. PATENT DOCUMENTS

| | | | |
|---|---|---|---|
| 5,510,158 | A | 4/1996 | Hiramoto et al. |
| 8,168,122 | B2 | 5/2012 | Lee |

(Continued)

FOREIGN PATENT DOCUMENTS

| | | | |
|---|---|---|---|
| CN | 1997773 | A | 7/2007 |
| CN | 103691246 | A | 4/2014 |

(Continued)

OTHER PUBLICATIONS

May 24, 2024 Office Action in Korean Patent Application Pub. No. 10-2022-7044636.

(Continued)

*Primary Examiner* — Xiuyu Tai
(74) *Attorney, Agent, or Firm* — Venable LLP

(57) ABSTRACT

An active oxygen supply device that is a plasma actuator equipped with a plasma generator and an ultraviolet light source in a housing having at least one opening, the plasma generator being provided with a first electrode and a second electrode with a dielectric in-between and creating an induced flow that contains ozone by applying a voltage between the two electrodes, in which the plasma actuator is positioned so that the induced flow flows outside the housing from an opening, and the ultraviolet light source irradiates the induced flow with ultraviolet rays and generates active
(Continued)

oxygen in the induced flow; a device for conducting treatment by active oxygen; and a method for conducting treatment by active oxygen.

6 Claims, 7 Drawing Sheets

(30) Foreign Application Priority Data

Apr. 26, 2021 (JP) ................................ 2021-074076
Jun. 7, 2021 (JP) ................................ 2021-094894

(58) Field of Classification Search
CPC .............. A61L 9/22; A61L 9/015; A61L 9/20; A61L 2103/50; A61L 2103/75; H01J 37/32; H01J 37/32715; H01J 37/32568; H01J 37/32834; H01J 37/32055; H01J 2237/335; B08B 7/0035; B08B 2203/005; B08B 9/0804; D06L 1/00; D06L 4/00; D06L 4/50; D06M 10/001; D06M 10/025; D06M 10/06; D06M 16/00; B03C 3/017; B03C 3/38; A61B 7/02; A61B 2562/245; H05H 1/2406; H05H 1/2425
See application file for complete search history.

(56) References Cited

U.S. PATENT DOCUMENTS

| | | | |
|---|---|---|---|
| 8,641,977 B2 | 2/2014 | Snowball | |
| 8,685,329 B2 | 4/2014 | Lee | |
| 9,005,531 B2 | 4/2015 | Mole | |
| 9,034,255 B2 | 5/2015 | Lee | |
| 9,119,892 B2 | 9/2015 | Mueller et al. | |
| 9,370,592 B2 | 6/2016 | Lee | |
| 9,597,422 B2 | 3/2017 | Snowball | |
| 10,188,766 B2 | 1/2019 | Lee | |
| 10,232,076 B2 | 3/2019 | Lee | |
| 10,940,223 B2 | 3/2021 | Lee | |
| 10,967,094 B2 | 4/2021 | Lee | |
| 11,207,436 B2 | 12/2021 | Lee | |
| 2005/0099134 A1 | 5/2005 | Harada | |
| 2005/0161433 A1 | 7/2005 | Silberberg et al. | |
| 2007/0119699 A1 | 5/2007 | Chambers et al. | |
| 2008/0260578 A1* | 10/2008 | Engemann | A61L 2/202 422/186.04 |
| 2009/0041617 A1 | 2/2009 | Lee | |
| 2010/0047116 A1 | 2/2010 | Garner | |
| 2011/0212185 A1 | 9/2011 | Tanaka et al. | |
| 2012/0063959 A1 | 3/2012 | Woodbridge | |
| 2012/0093691 A1 | 4/2012 | Mole | |
| 2012/0111359 A1 | 5/2012 | Mueller et al. | |
| 2012/0148445 A1 | 6/2012 | Makoto et al. | |
| 2012/0183444 A1 | 7/2012 | Lee | |
| 2012/0288405 A1 | 11/2012 | Snowball | |
| 2014/0065013 A1 | 3/2014 | Nonnenmacher | |
| 2014/0119991 A1 | 5/2014 | Snowball | |
| 2014/0154133 A1 | 6/2014 | Lee | |
| 2015/0196675 A1 | 7/2015 | Lee | |
| 2015/0273092 A1 | 10/2015 | Holub et al. | |
| 2015/0273093 A1 | 10/2015 | Holub et al. | |
| 2016/0287737 A1 | 10/2016 | Lee | |
| 2017/0144891 A1 | 5/2017 | Haruyama | |
| 2018/0185538 A1 | 7/2018 | Lee et al. | |
| 2019/0060500 A1 | 2/2019 | Lee | |
| 2019/0167832 A1 | 6/2019 | Lee | |
| 2019/0322107 A1 | 10/2019 | Ozawa et al. | |
| 2021/0185793 A1 | 6/2021 | Wu et al. | |
| 2021/0187143 A1 | 6/2021 | Lee | |
| 2021/0308316 A1 | 10/2021 | Lee | |
| 2022/0072176 A1 | 3/2022 | Lee | |

FOREIGN PATENT DOCUMENTS

| | | | |
|---|---|---|---|
| CN | 103977439 A | 8/2014 | |
| CN | 106390702 A | 2/2017 | |
| EP | 2411058 B1 | 5/2015 | |
| JP | S52-3872 A | 1/1977 | |
| JP | S64-25865 A | 1/1989 | |
| JP | S64-25866 A | 1/1989 | |
| JP | H10-328279 A | 12/1998 | |
| JP | H11-090370 A | 4/1999 | |
| JP | 3062251 U | 9/1999 | |
| JP | 2005-336492 A | 12/2005 | |
| JP | 2009-517175 A | 4/2009 | |
| JP | 2012-521240 A | 9/2012 | |
| JP | 2013-154145 A | 8/2013 | |
| JP | 2013-158706 A | 8/2013 | |
| JP | 2014-061418 A | 4/2014 | |
| JP | 2014-516013 A | 7/2014 | |
| JP | 2015-085297 A | 5/2015 | |
| JP | 2017-518948 A | 7/2017 | |
| KR | 10-1995-0014015 A | 6/1995 | |
| KR | 2017-0026482 A | 3/2017 | |
| KR | 10-2007-0039824 A | 4/2017 | |
| KR | 101769806 B1 | 8/2017 | |
| KR | 2018-0017425 A | 2/2018 | |
| WO | 2010/032765 A | 3/2010 | |
| WO | 2015/198608 A | 12/2015 | |
| WO | 2017/110502 A1 | 6/2017 | |
| WO | 2017/183781 A1 | 10/2017 | |

OTHER PUBLICATIONS

Jul. 19, 2024 Extended Search Report in European Patent Application Pub. No. 21 832 011.7.
Jul. 31, 2024 Office Action in Korean Patent Application Pub. No. 10-2022-7044633.
Feb. 28, 2025 Office Action in Chinese Patent Application No. 202180046672.4 (with English translation).
Apr. 28, 2025 Notice of Allowance in Korean atent Application No. 10-2022-7044633.
Jan. 16, 2025 Office Action in Korean Patent Application Pub. No. 10-2022-7044636.
Dec. 20, 2024 extended European Search Report European Patent Application No. 21 831 495.3.
Jul. 8, 2025 Office Action in Japanese Patent Application Pub. No. 2021-095018.
Apr. 26, 2024 Office Action in Chinese Patent Application Pub. No. 202180046623.0 (with English translation).
Mar. 29, 2022 Office Action in Japanese Patent Application Pub. No. 2021-094894.
International Search Report and Written Opinion of the International Searching Authority for International Patent Application No. PCT/JP2021/024688.

* cited by examiner

ACTIVE OXYGEN SUPPLY DEVICE, DEVICE FOR CONDUCTING TREATMENT BY ACTIVE OXYGEN, AND METHOD FOR CONDUCTING TREATMENT BY ACTIVE OXYGEN

CROSS-REFERENCE TO RELATED APPLICATION

This is a continuation of International Application No. PCT/JP2021/024688, filed on Jun. 30, 2021, and designated the U.S., and claims priority from Japanese Patent Application No. 2020-113518 filed on Jun. 30, 2020, Japanese Patent Application No. 2020-176934 filed on Oct. 21, 2020, Japanese Patent Application No. 2021-074076 filed on Apr. 26, 2021, and Japanese Patent Application No. 2021-094894 filed on Jun. 7, 2021, the entire contents of which are incorporated herein by reference.

BACKGROUND OF THE INVENTION

Field of the Invention

The present disclosure relates to an active oxygen supply device, a device for treatment with active oxygen, and a method for treatment with active oxygen.

Description of the Related Art

Ultraviolet light and ozone are known as means for sterilizing articles and the like. Japanese Patent Application Publication No. H01-25865 discloses a method using a sterilization device having an ozone supply device, an ultraviolet light generating lamp, and an agitating device to sterilize even the shaded portions of a sample by agitating active oxygen generated by irradiating ozone with ultraviolet light emitted by the ultraviolet light generating lamp, thereby solving the problem that sterilization by ultraviolet light is limited to a portion of an object to be sterilized that is irradiated with the ultraviolet light.

SUMMARY OF THE INVENTION

At least one aspect of the present disclosure is directed to providing an active oxygen supply device capable of more efficiently supplying active oxygen to the surface of an object to be treated, a device for treatment with active oxygen that is capable of more efficiently treating the surface of the object to be treated with active oxygen, and a method for treatment with active oxygen that is capable of more efficiently treating the surface of the object to be treated with active oxygen.

According to at least one aspect of the present disclosure, there is provided an active oxygen supply device comprising a plasma generator and an ultraviolet light source in a housing having at least one opening,

- the plasma generator being a plasma actuator that is provided with a first electrode and a second electrode with a dielectric in-between, and that generates an induced flow including ozone by applying a voltage between the two electrodes,
- the plasma actuator being arranged so that the induced flow flows out of the housing from the opening, and
- the ultraviolet light source irradiating the induced flow with ultraviolet light and generating active oxygen in the induced flow.

Also, according to at least one aspect of the present disclosure, there is provided a device for treating a surface of an object to be treated with active oxygen, wherein

- the device comprises a plasma generator and an ultraviolet light source in a housing having at least one opening
- the plasma generator is a plasma actuator that is provided with a first electrode and a second electrode with a dielectric in-between, and that generates an induced flow including ozone by applying a voltage between the two electrodes,
- the plasma actuator is arranged so that the induced flow flows out of the housing from the opening, and
- the ultraviolet light source irradiates the induced flow with ultraviolet light and generates active oxygen in the induced flow.

Further, according to at least one aspect of the present disclosure, there is provided a treatment method for treating a surface of an object to be treated with active oxygen, comprising:

- a step of providing a device for treatment with active oxygen comprising a plasma generator and an ultraviolet light source in a housing having at least one opening,
- the plasma generator being a plasma actuator that is provided with a first electrode and a second electrode with a dielectric in-between, and that generates an induced flow including ozone by applying a voltage between the two electrodes, the plasma actuator being arranged so that the induced flow flows out of the housing from the opening, and the ultraviolet light source irradiating the induced flow with ultraviolet light and generating active oxygen in the induced flow;
- a step of placing the device for treatment with active oxygen and the object to be treated at relative positions such that a surface of the object to be treated is exposed when the induced flow is caused to flow from the opening; and
- a step of causing the induced flow to flow from the opening to treat the surface of the object to be treated with active oxygen.

According to one embodiment of the present disclosure, it is possible to obtain an active oxygen supply device capable of more efficiently supplying active oxygen to the surface of an object to be treated, a device for treatment with active oxygen that is capable of more efficiently treating the surface of the object to be treated with active oxygen, and a method for treatment with active oxygen that is capable of more efficiently treating the surface of the object to be treated with active oxygen. Further features of the present disclosure will become apparent from the following description of exemplary embodiments with reference to the attached drawings.

DESCRIPTION OF THE EMBODIMENTS

Figure 1:
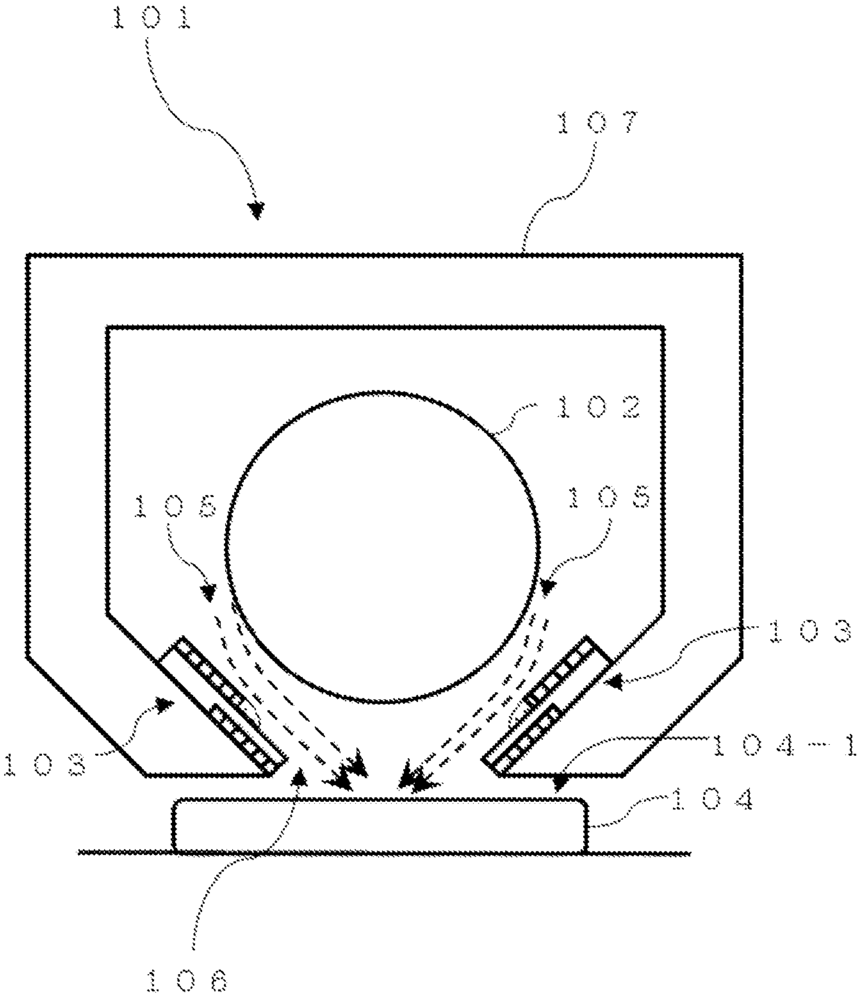
FIG. 1 is schematic cross-sectional view showing the configuration of an active oxygen supply device according to one embodiment of the present disclosure.

Hereinafter, specific examples of embodiments for carrying out the present disclosure will be described with reference to the drawings. However, the dimensions, materials, shapes, and relative arrangement of the components described in the embodiments should be changed, as appropriate, according to the configuration of the members to which the disclosure is applied and various conditions. That is, the scope of the present disclosure is not intended to be limited to the following embodiments.

In addition, in the present disclosure, the descriptions of "XX or more and YY or less" or "XX to YY" representing numerical ranges mean numerical ranges including the lower and upper limits, which are endpoints, unless otherwise specified. When numerical ranges are stated stepwise, the upper and lower limits of each numerical range can be combined arbitrarily.

Further, "bacteria" as the object of "sterilization" according to the present disclosure refers to microorganisms, and the microorganisms include fungi, bacteria, unicellular algae, viruses, protozoa, and the like, as well as animal or plant cells (stem cells, dedifferentiated cells and differentiated cells), tissue cultures, fused cells obtained by genetic engineering (including hybridomas), dedifferentiated cells, and transformants (microorganisms). Examples of viruses include, for example, norovirus, rotavirus, influenza virus, adenovirus, coronavirus, measles virus, rubella virus, hepatitis virus, herpes virus, HIV virus, and the like. Examples of bacteria include *Staphylococcus, Escherichia coli, Salmonella, Pseudomonas aeruginosa, Vibrio cholerae, Shigella, Anthrax, Mycobacterium tuberculosis, Clostridium botulinum, Tetanus, Streptococcus*, and the like. Furthermore, examples of fungi include *Trichophyton, Aspergillus, Candida*, and the like.

Furthermore, in the following explanation, configurations having the same functions are given the same numbers in the drawings, and description thereof may be omitted.

Furthermore, in the present description, the active oxygen supply device of the present disclosure and the device for treatment with active oxygen of the present disclosure are collectively referred to simply as "active oxygen supply device".

When the present inventors studied the sterilization performance of the sterilization method according to Japanese Patent Application Publication No. H01-25865, there were cases where the sterilization performance was about the same as that of the conventional sterilization method using only ozone. Since it is said that the sterilization ability of active oxygen is intrinsically far superior to that of ozone, such a study result was unexpected.

According to the study of the present inventors, the reason why the sterilization ability of the sterilization device according to Japanese Patent Application Publication No. H01-25865 is limited is presumed to be as follows.

In Japanese Patent Application Publication No. H01-25865, ozone is excited by irradiation with ultraviolet light to generate active oxygen with extremely high sterilization power. Here, active oxygen is a general term for highly reactive oxygen active species such as superoxide anion radicals (•$O_2^-$) and hydroxyl radicals (•OH). Due to high own reactivity thereof, active oxygen can instantly oxidize and decompose bacteria and viruses.

However, since ozone ab sorbs ultraviolet light very well, in the sterilization device according to Japanese Patent Application Publication No. H01-25865, generation of active oxygen is considered to be limited to the vicinity of the ultraviolet light generating lamp. That is, it is considered that the ultraviolet light does not sufficiently reach the ozone present at a position distant from the ultraviolet light generating lamp, and active oxygen is hardly generated at a position distant from the ultraviolet light generating lamp.

In addition, active oxygen is extremely unstable, with a half-life of $10^{-6}$ sec for •$O_2^-$ and a half-life of $10^{-9}$ sec for •OH, which are rapidly converted into stable oxygen and water. Therefore, it is considered difficult to passively fill the interior of the body of the sterilization device with active oxygen generated in the vicinity of the ultraviolet light generating lamp. In other words, it is considered that the sterilization by the sterilization method according to Japanese Patent Application Publication No. H01-25865 is substantially performed by ozone. Therefore, it is considered that the sterilization performance of the sterilization method according to Japanese Patent Application Publication No. H01-25865 is about the same as the sterilization performance of the conventional sterilization method using only ozone.

Based on these considerations, the present inventors have recognized that when treating an object to be treated using active oxygen, which has a short life, it is necessary to place the object to be treated or the surface to be treated more actively in an active oxygen atmosphere. The results of studies conducted by the present inventors based on such recognition have demonstrated that with the active oxygen supply device described below, the object to be treated can be placed in an active oxygen atmosphere more actively. In the present disclosure, the "treatment" of the object to be treated with active oxygen is inclusive of various types of treatment that can be accomplished by active oxygen, such as surface modification (hydrophilization treatment), sterilization, deodorization, bleaching, and the like of the surface of the object to be treated with active oxygen.

An active oxygen supply device 101 according to one embodiment of the present disclosure will be described below with reference to FIG. 1. The active oxygen supply device 101 according to one embodiment of the present disclosure includes an ultraviolet light source 102 and a plasma generator 103 inside a housing 107 having at least one opening 106.

The ultraviolet light source 102 irradiates the induced flow 105 with ultraviolet light to generate active oxygen in the induced flow 105. In FIG. 1, reference numeral 104 denotes an object to be treated.

Figure 2:
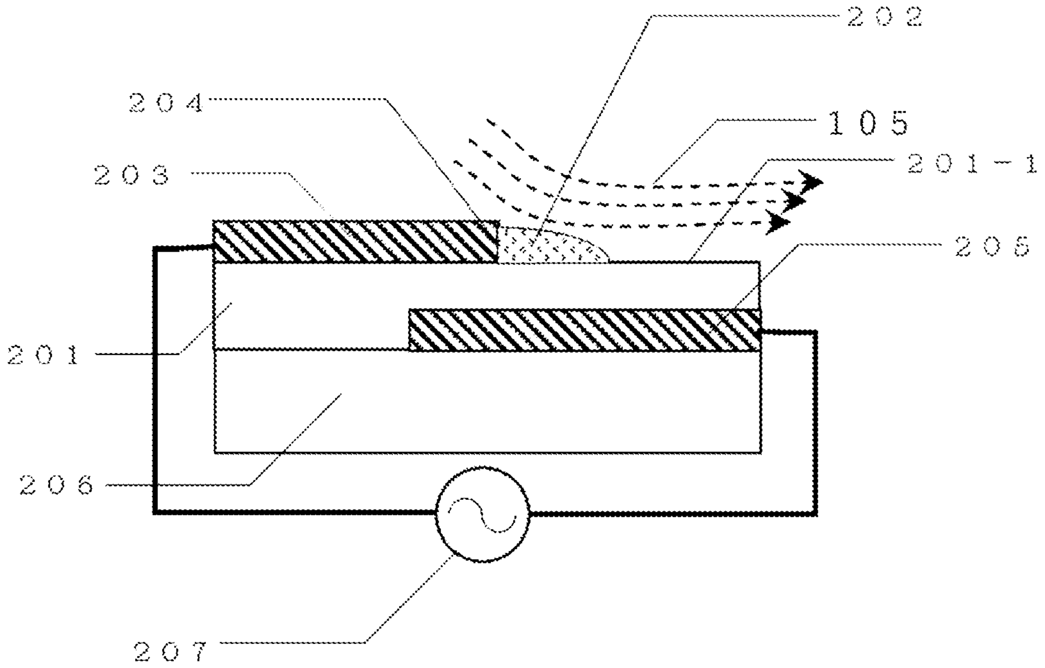
FIG. 2 is a schematic cross-sectional view showing the configuration of a plasma generator according to one embodiment of the present disclosure.

A cross-sectional structure of one embodiment of the plasma generator 103 is shown in FIG. 2. The plasma generator is a so-called dielectric barrier discharge (DBD) plasma actuator (hereinafter sometimes simply referred to as "DBD-PA") in which a first electrode 203 is provided on one surface (hereinafter referred to as "first surface") of a dielectric 201 and a second electrode 205 provided on a surface (hereinafter referred to as "second surface") opposite to the first surface. In FIG. 2, reference numeral 206 denotes a dielectric substrate, and reference numeral 207 denotes a power source.

In the plasma generator 103, the first electrode 203 and the second electrode 205, which are arranged with the dielectric 201 in-between, are obliquely arranged with a shift. By applying a voltage between these electrodes (between both electrodes), plasma 202 is generated from the first electrode 203 toward the second electrode 205, and a jet-like flow is induced by the surface plasma 202 from an edge 204 of the first electrode 203 along the exposed portion (the portion not covered with the first electrode) 201-1 of the first surface of the dielectric 201. At the same time, a suction flow of air is generated from the space within the container toward the electrodes. Electrons in the surface plasma 202 collide with oxygen molecules in the air thereby causing dissociation of the oxygen molecules and producing oxygen atoms. The generated oxygen atoms collide with undissociated oxygen molecules to generate ozone. Therefore, due to the action of the jet-like flow created by the surface plasma 202 and the suction flow of air, an induced flow 105 including high-concentration ozone is generated from the edge 204 of the first electrode 203 along the surface of the dielectric 201.

The plasma generator 103 is arranged so that the induced flow 105 flows out of the housing 107 from the opening 106 and is supplied to a treatment surface 104-1 of the object 104 to be treated.

That is, in the active oxygen supply device according to one embodiment of the present disclosure, the induced flow 105 including ozone from the plasma generator 103 flows out of the housing 107 from the opening 106 and is supplied to the treatment surface 104-1 of the object 104 to be treated. The induced flow 105 is irradiated with ultraviolet light by the ultraviolet light source 102 to generate active oxygen in the induced flow 105, thereby making it possible to actively supply active oxygen to a region close to the treatment surface 104-1, specifically, to a spatial region (hereinafter also referred to as a "surface region") with a height of, for example, up to about 1 mm from the treatment surface. Therefore, the generated active oxygen can be supplied to the surface of the object to be treated before the active oxygen is converted into oxygen and water. As a result, the treatment surface 104-1 of the object 104 to be treated is more reliably treated with active oxygen.

<Electrodes and Dielectric>

The material for forming the first electrode and the second electrode is not particularly limited as long as it is a highly conductive material. For example, metals such as copper, aluminum, stainless steel, gold, silver, and platinum, materials plated or vapor-deposited therewith, conductive carbon materials such as carbon black, graphite, and carbon nanotubes, composite materials which are mixtures thereof with resins and the like can be used. The material forming the first electrode and the material forming the second electrode may be the same or different.

Among these, from the viewpoint of avoiding electrode corrosion and achieving uniform discharge, it is preferable that the material constituting the first electrode be aluminum, stainless steel, or silver. For the same reason, the material constituting the second electrode is also preferably aluminum, stainless steel, or silver.

In addition, the shape of the first electrode and the second electrode can be plate-like, wire-like, needle-like, or the like, without particular limitation. Preferably, the shape of the first electrode is flat. Further, preferably, the shape of the second electrode is flat. When at least one of the first electrode and the second electrode is flat, the flat plate preferably has an aspect ratio (long side length/short side length) of 2 or more.

At least one of the first electrode and the second electrode preferably has an apex angle of 45° or less (that is, the electrode is sharp), but this feature is not limiting. Although the drawings show the case where the apex angles of the first electrode and the second electrode are both 90°, the present disclosure is also inclusive of an embodiment in which the apex angle exceeds 45°.

The dielectric is not particularly limited as long as it is a material with high electrical insulation. For example, resins such as polyimides, polyesters, fluororesins, silicone resins, acrylic resins, and phenolic resins, glass, ceramics, and composite materials which are mixtures thereof with resins can be used. Among these, it is preferable that the dielectric be a ceramic material or glass because fire is unlikely to spread even if the current leaks.

<Plasma Actuator>

The plasma actuator is not particularly limited as long as an induced flow including ozone can be generated by providing a first electrode and a second electrode with a dielectric in-between and applying a voltage between the electrodes. In the plasma actuator, the shorter the shortest distance between the first electrode and the second electrode, the easier plasma is generated. Therefore, the thickness of the dielectric is preferably as small as possible as long as no electrical breakdown occurs, and can be 10 μm to 1000 μm, preferably 10 μm to 200 μm. Also, the shortest distance between the first electrode and the second electrode is preferably 200 μm or less.

Figure 3:
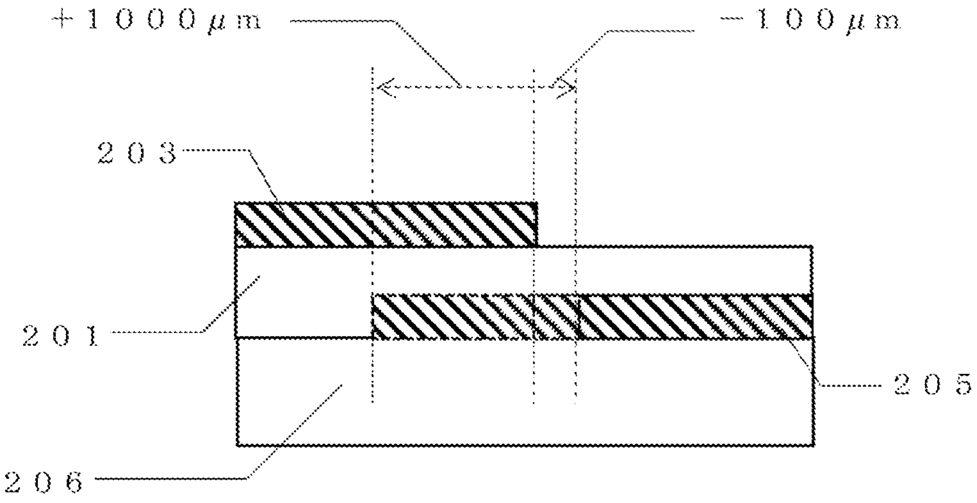
FIG. 3 is an explanatory drawing of a plasma actuator according to one embodiment of the present disclosure.

FIG. 3 is an explanatory diagram of the overlap between the first electrode 203 and the second electrode 205 of the plasma actuator, which is an ozone generator. This is a cross-sectional view of the plasma actuator.

In the first electrode 203 and the second electrode 205 arranged obliquely opposite each other, the edge of the first electrode may be present at the portion where the second electrode is formed with the dielectric in-between, when viewed from the upper side of the cross-sectional view. That is, the first electrode and the second electrode may be provided so as to overlap each other with the dielectric in-between. In this case, it is preferable to prevent dielectric breakdown at the time of voltage application in the portion where the first electrode and the second electrode overlap each other with the dielectric in-between.

Also, when the first electrode and the second electrode are separated from each other when viewed from the top of the cross-sectional view, it is preferable to increase the voltage in order to compensate for the weakening of the electric field due to the increased distance between the electrodes. The overlap between the edge of the first electrode and the edge of the second electrode is more preferably −100 μm to +1000 μm when viewed from the top of the cross-sectional view, assuming that the overlapping length is positive.

The thickness of the electrodes is not particularly limited for both the first electrode and the second electrode and can be 10 μm to 1000 μm. When the thickness is 10 μm or more, the resistance becomes low and plasma is easily generated. When the thickness is 1000 μm or less, electric field concentration is likely to occur, and plasma is likely to be generated.

The width of the electrodes is not particularly limited for both the first electrode and the second electrode and can be 1000 μm or more.

Further, when the edge of the second electrode is exposed, plasma is also generated from the edge of the second electrode, and an induced flow can be generated in the opposite direction to the induced flow 105 derived from the first electrode. In the active oxygen supply device according to the present embodiment, it is preferable that the ozone concentration in the internal space of the active oxygen supply device other than the surface region of the object to be treated be kept as low as possible. Moreover, it is preferable not to generate a gas flow in the container that disturbs the flow of the induced flow 105. Therefore, it is preferable not to generate an induced flow derived from the second electrode. For this purpose, it is preferable that the second electrode 205 be covered with a dielectric such as the dielectric substrate 206, as shown in FIGS. 2 and 3, or embedded in the dielectric 201 to prevent plasma generation from the edges of the second electrode.

The induced flow 105 including high-concentration ozone flows in the direction of jet-like flow induced by surface plasma from the edge 204 of the first electrode 203 along the exposed portion 201-1 of the first surface of the dielectric 201, that is, in the direction from the edge 204 of the first electrode 203 along the exposed portion 201-1 of the first surface of the dielectric. This induced flow is a flow of gas including high-concentration ozone and having a velocity of several m/s to several tens of m/s.

The voltage applied between the first electrode 203 and the second electrode 205 of the plasma actuator is not particularly limited as long as plasma can be generated in the plasma actuator. Further, the voltage may be a DC voltage or an AC voltage, but an AC voltage is preferred. Moreover, in a preferable embodiment, the voltage is a pulse voltage.

Furthermore, the amplitude and frequency of the voltage can be set, as appropriate, to adjust the flow velocity of the induced flow and the ozone concentration in the induced flow. In this case, the selection may be made, as appropriate, from the viewpoint of generating the effective active oxygen concentration or the ozone concentration required to generate the effective active oxygen amount corresponding to the purpose of the treatment in the induced flow, and supplying the generated active oxygen to the surface region of the object to be treated while maintaining the active oxygen concentration or the effective active oxygen amount corresponding to the purpose of the treatment.

For example, the amplitude of the voltage can be 1 kV to 100 kV. Furthermore, the frequency of the voltage is preferably 1 kHz or higher, more preferably 10 kHz to 100 kHz.

When the voltage is an alternating voltage, the waveform of the alternating voltage is not particularly limited, and a sine wave, a rectangular wave, a triangular wave, or the like can be used, but a rectangular wave is preferable from the viewpoint of the rapid rise of the voltage.

The duty ratio of the voltage can also be selected as appropriate, but it is preferable that the voltage rises quickly. Preferably, the voltage is applied so that the rise of the voltage from the bottom to the peak of the amplitude of the wavelength is 400,000 V/sec or more.

The value obtained by dividing the amplitude of the voltage applied between the first electrode 203 and the second electrode 205 by the film thickness of the dielectric 201 (voltage/film thickness) is preferably 10 kV/mm or more.

<Ultraviolet Light Source and Ultraviolet Light>

The ultraviolet light source is not particularly limited as long as ultraviolet light that can excite ozone and generate active oxygen can be emitted. Further, the ultraviolet light source is not particularly limited as long as the wavelength and illuminance of ultraviolet light required to excite ozone and obtain the effective active oxygen concentration or the effective active oxygen amount corresponding to the purpose of the treatment can be obtained.

Since the peak value of the light absorption spectrum of ozone is 260 nm, for example, the peak wavelength of the ultraviolet light is preferably 220 nm to 310 nm, more preferably 253 nm to 285 nm, and even more preferably 253 nm to 266 nm.

Examples of specific ultraviolet light sources that can be used include low-pressure mercury lamps in which mercury is enclosed in quartz glass together with an inert gas such as argon or neon, cold cathode tube ultraviolet lamps (UV-CCL), ultraviolet LEDs, and the like. The wavelength of the low-pressure mercury lamp and the cold-cathode tube ultraviolet lamp may be selected from 254 nm or the like. Meanwhile, the wavelength of the ultraviolet LED may be selected from 265 nm, 275 nm, 280 nm, and the like from the viewpoint of output performance.

<Arrangement of Plasma Generator, Ultraviolet Light Source and Object to be Treated>

In the active oxygen supply device 101, the position of the plasma generator 103 that generates the induced flow including ozone is not particularly limited provided that the plasma generator is arranged so that the induced flow 105 flows out of the housing from the opening and is supplied to the surface of the object to be treated in a state in which the effective active oxygen concentration or the effective active oxygen amount corresponding to the purpose of the treatment is maintained by the ultraviolet light emitted from the ultraviolet light source 102.

For example, the plasma generator and the ultraviolet light source may be arranged so that the induced flow 105 including active oxygen generated by ultraviolet light is supplied to the surface of the object to be treated in the shortest distance.

Further, for example, the arrangement may be such that the treatment surface 104-1 of the object to be treated is included on the extension line from the edge of the first electrode of the plasma actuator in the direction along the exposed portion 201-1 of the first surface of the dielectric.

Furthermore, a narrow angle θ (hereinafter also referred to as plasma actuator incident angle or PA incident angle. See FIG. 4) formed by an extension line 201-1-1 from the edge of the first electrode of the plasma actuator in the direction along the exposed portion 201-1 of the first surface of the dielectric and the horizontal plane (plane perpendicular to the vertical direction) when the opening of the active oxygen supply device is directed vertically downward is not particularly limited as long as the angle makes it possible to supply actively the induced flow to the surface region of the object to be treated or to perform treatment with active oxygen in a state in which the effective active oxygen concentration or the effective active oxygen amount corresponding to the purpose of the treatment is maintained, but is preferably 0° to 90° and more preferably 30° to 70°.

By arranging the plasma generator and the ultraviolet light source as described above, an induced flow including active oxygen and having a certain flow velocity can be locally supplied to a region near the surface of the object to be treated, or treatment with the active oxygen can be performed.

The ultraviolet light source is not particularly limited as long as the ultraviolet light source is arranged so that the induced flow is irradiated with ultraviolet light, active oxygen is generated in the induced flow, and the treatment at the surface of the object to be treated can be performed in a state in which the effective active oxygen concentration or the effective active oxygen amount corresponding to the purpose of the treatment is maintained.

As described above, the induced flow including ozone is actively supplied to the region near the surface of the object to be treated. Also, by irradiating the induced flow with ultraviolet light, active oxygen can be generated in the induced flow. Therefore, by irradiating the induced flow with ultraviolet light, ozone is excited and the induced flow in which active oxygen is generated can be actively supplied to the surface of the object to be treated. Further, the active oxygen concentration or active oxygen amount on the surface of the object to be treated can be significantly increased.

The relative positions of the ultraviolet light source and the plasma generator are not particularly limited as long as the ultraviolet light source and the plasma generator are arranged so that active oxygen is generated in the induced flow and the treatment at the surface of the object to be treated can be performed in a state in which the effective active oxygen concentration or the effective active oxygen amount corresponding to the purpose of the treatment is maintained.

Further, since the distance between the ultraviolet light source and the plasma generator changes depending on the purpose of the treatment, this distance cannot be defined unconditionally, but for example, it is preferably 10 mm or less, more preferably 4 mm or less. However, it is not necessary to place the plasma generator within about 10 mm from the ultraviolet light source, and the distance between the ultraviolet light source and the plasma generator is not particularly limited as long as the concentration of active oxygen in the induced flow can be set to an effective value corresponding to the purpose of the treatment based on the relationship with the illuminance or wavelength of ultraviolet light, which will be described hereinbelow.

It is also a preferred embodiment to provide a moving means for at least one of the ultraviolet light source and the plasma generator so that at least one of the ultraviolet light source and the plasma generator be movable to ensure uniform illuminance of the ultraviolet light.

As for the relative positions of the active oxygen supply device and the object to be treated, at least one thereof may be arranged so that active oxygen is generated in the induced flow and the surface of the object to be treated is exposed to the induced flow in which the effective active oxygen concentration or the effective active oxygen amount corresponding to the purpose of the treatment is maintained.

Further, the ultraviolet light source may be arranged at a position where the surface of the object to be treated can be irradiated with ultraviolet light, or may be arranged at a position where the surface of the object to be treated cannot be irradiated with ultraviolet light. Even when the surface of the object to be treated cannot be irradiated with ultraviolet light from the ultraviolet light source, if the device for treatment with active oxygen according to the present embodiment is used, the treatment can be performed by exposing the surface to be treated to active oxygen in the induced flow. Furthermore, in the sterilization treatment with ultraviolet light, only the surface irradiated with ultraviolet light is sterilized. However, in the sterilization treatment by the active oxygen supply device according to the present disclosure, it is possible to sterilize bacteria present at the position that can be reached by active oxygen. Therefore, for example, it is possible to sterilize even bacteria present between fibers, which are difficult to sterilize by ultraviolet irradiation from the outside.

Meanwhile, when the arrangement is such that the surface of the object to be treated that is placed outside the housing can be irradiated by ultraviolet light from the ultraviolet light source through the opening, the undecomposed ozone present in the induced flow is decomposed in situ on the surface to be treated and active oxygen can be generated on the surface to be treated. As a result, the degree of treatment and the efficiency of treatment can be further enhanced.

In this case, the illuminance of the ultraviolet light on the surface of the object to be treated or the illuminance of the ultraviolet light on the opening is not particularly limited, but it is preferable that even on the surface of the object to be treated or the opening, the illuminance of ultraviolet light be set, for example, such that ozone contained in the induced flow is decomposed, active oxygen is generated in the induced flow, and the effective active oxygen concentration or the effective active oxygen amount corresponding to the purpose of the treatment can be generated. Specifically, for example, as a specific example of the ultraviolet illuminance on the surface of the object to be treated or the ultraviolet illuminance on the opening, it is preferably 40 $\mu W/cm^2$ or more, more preferably 100 $\mu W/cm^2$ or more, even more preferably 400 $\mu W/cm^2$ or more, and particularly preferably 1000 $\mu W/cm^2$ or more. Although the upper limit of the illuminance is not particularly limited, it can be, for example, 10,000 $\mu W/cm^2$ or less.

Furthermore, since the distance between the ultraviolet light source and the surface of the object to be treated also changes depending on the purpose of the treatment, it cannot be defined unconditionally, but for example, this distance is preferably 10 mm or less, more preferably 4 mm or less. However, it is not necessary to place the object to be treated so that the surface to be treated is within about 10 mm from the ultraviolet light source, and the distance between the ultraviolet light source and the object to be treated is not particularly limited as long as the concentration of active oxygen in the induced flow can be set to an effective value corresponding to the purpose of the treatment based on the relationship with the illuminance or the like of ultraviolet light.

Also, the amount of ozone generated per unit time in a state in which the induced flow is not irradiated with ultraviolet light in the plasma actuator is preferably, for example, 15 μg/min or more. More preferably, it is 30 μg/min or more. The upper limit of the ozone generation amount is not particularly limited, but is, for example, 1000 μg/min or less.

The flow velocity of the induced flow may be, for example, such that the generated active oxygen can be actively supplied to the surface region of the object to be treated in a state in which the effective active oxygen concentration or the effective active oxygen amount corresponding to the purpose of the treatment is maintained. For example, the flow velocity is about 0.01 m/s to 100 m/s as described above.

As described above, the concentration of ozone in the induced flow generated by the plasma actuator and the flow velocity of the induced flow can be controlled by the thickness and material of the electrodes and dielectric, and the type, amplitude, frequency and the like of the applied voltage.

<Housing and Opening>

The active oxygen supply device of the present disclosure comprises the housing 107 having at least one opening 106, the ultraviolet light source 102 arranged in the housing, and the plasma generator 103.

The opening is not particularly limited as long as the induced flow 105 generated from the plasma generator 103 is allowed to flow out of the housing 107. The size of the opening, the position of the opening, and the relative positions of the opening and the object to be treated can be selected, as appropriate, so that the generated active oxygen can be actively supplied to the surface region of the object to be treated in a state in which the effective active oxygen concentration or the effective active oxygen amount corresponding to the purpose of the treatment is maintained.

The active oxygen supply device of the present disclosure can be used not only for sterilization of objects to be treated, but also for general applications implemented by supplying active oxygen to the objects to be treated. For example, the active oxygen supply device of the present disclosure can be used for deodorizing the object to be treated, bleaching the object to be treated, hydrophilizing the surface of the object to be treated, and the like.

In addition, the device for treatment with active oxygen of the present disclosure can be used not only for performing the treatment of sterilizing objects to be treated, but for example, for the treatment of deodorizing the object to be treated, the treatment of bleaching the object to be treated, the surface treatment of hydrophilizing the object to be treated, and the like.

In the present disclosure, “effective active oxygen concentration or effective active oxygen amount” means the active oxygen concentration or active oxygen amount for achieving the purpose related to the object to be treated, such as sterilization, deodorization, bleaching or hydrophilization, and can be adjusted, as appropriate, according to the purpose by using the electrodes constituting the plasma actuator, the thickness and material of the dielectric, the type, amplitude and frequency of the voltage to be applied, the illuminance and irradiation time of ultraviolet light, the PA incident angle, and the like.

EXAMPLES

The present disclosure will be described in more detail below using Examples and Comparative Examples, but the embodiments of the present disclosure are not limited to these.

Example 1

1. Production of Active Oxygen Supply Device

The first electrode was formed by attaching an aluminum foil having a length of 2.5 mm, a width of 15 mm, and a thickness of 100 μm to the first surface of a glass plate (length 5 mm, width 18 mm (the depth direction of the paper surface in FIG. 1), thickness 150 μm) as a dielectric with a pressure-sensitive adhesive tape. Further, the second electrode was formed by attaching an aluminum foil having a length of 3 mm, a width of 15 mm, and a thickness of 100 μm to the second surface of the glass plate with a pressure-sensitive adhesive tape so as to obliquely face the aluminum foil attached to the first surface. Additionally, the second surface including the second electrode was covered with a polyimide tape. In this way, a plasma actuator was produced in which the first electrode and the second electrode were provided so as to overlap each other over a width of 0.5 mm with the dielectric (glass plate) disposed in-between. Two such plasma actuators were prepared.

Next, a case made of ABS resin and having a height of 25 mm, a width of 20 mm, a length of 170 mm, a thickness of 2 mm, and a substantially trapezoidal cross-sectional shape as shown in FIG. 1 was prepared as the housing 107 of the active oxygen supply device 101. The case had an opening 106 with a width of 7 mm and a length of 166 mm on one side. Next, the two previously produced plasma actuators were fixed to the inner walls of the oblique side portions of the housing 107. Specifically, the plasma actuator 103 was positioned so that the angle θ at the intersection of the extension line 201-1-1 in the direction along the exposed portion 201-1 of the first surface of the dielectric 201 and the treatment surface 104-1 of the object to be treated (the same value as the PA incident angle described above) was 45°. Furthermore, an ultraviolet lamp 102 (cold-cathode tube ultraviolet lamp, trade name: UW/9F89/9, manufactured by Stanley Electric Co., Ltd., cylindrical shape with a diameter of 9 mm, peak wavelength=254 nm) was arranged in the housing. The arrangement was such that the distance (reference numeral 403 in FIG. 4) between the ultraviolet lamp 102 and the exposed portion 201-1 of the first surface of the dielectric 201 of the plasma actuator was 2 mm and the distance (reference numeral 401 in FIG. 4) between the ultraviolet light source and the surface of the flat plate facing the ultraviolet light source was 3 mm when the flat plate was brought into contact with the opening 106 of the housing 107. An active hydrogen supply device (a device for treatment with active oxygen) according to the present example was thus produced.

An illuminance meter (trade name: spectral irradiance meter USR-45D, manufactured by Ushio Inc.) was placed at the position of the opening 106 serving as an active oxygen supply port in the active oxygen supply device 101 to measure the illuminance of ultraviolet light. From the integrated value of the spectrum, the illuminance was 1370 $\mu W/cm^2$. At this time, the power to the plasma actuator was not turned on so as to avoid the effect of shielding the ultraviolet light by ozone generated from the plasma actuator. Since the object to be treated was placed, for example, at the position of the opening 106, the illuminance of ultraviolet light measured under these conditions was regarded as the illuminance of ultraviolet light on the surface of the object to be treated.

Subsequently, in order to calculate the amount of ozone generated from the plasma actuator 103, the active oxygen supply device 101 was placed in a sealed container (not shown) with a volume of 1 liter. The sealed container was provided with a hole that could be sealed with a rubber plug, and the internal gas could be sucked through the hole with a syringe. One minute after applying a voltage having a sine waveform with an amplitude of 2.4 kV and a frequency of 80 kHz to the plasma actuator 103, 100 ml of the gas in the sealed container was sampled. The sampled gas was sucked into an ozone detection tube (trade name: 182SB, manufactured by Komyo Rikagaku Kogyo K.K.), and the measured ozone concentration (PPM) contained in the induced flow from the plasma actuator 103 was measured. Using the measured ozone concentration value, the amount of ozone generated per unit time was obtained from the following equation.

[Math. 1]

$$\text{Amount of ozone generated per unit}\left(\frac{\text{mg}}{\text{min}}\right) = \text{Measured ozone concentration } (PPM) * \frac{\text{Molecular weight of ozone 48}}{22.4} *$$

-continued $$\frac{\frac{273}{273+\text{Room temperature }(^\circ\text{ C.})}}{10000} * \frac{\text{Gas in sealed container (L)}}{\text{Sampled gas(L)}} =$$

$$\text{Measured ozone concentration }(PPM)*48/22.4*273/(273+25)/10000*0.1/1$$

As a result, the amount of ozone generated per unit time was 39 μg/min. At this time, the ultraviolet light source was not turned on so as to avoid the effect of the decomposition of ozone by the ultraviolet light emitted from the ultraviolet light source.

Finally, the amount of ozone generated was measured when both the plasma actuator 103 and the ultraviolet lamp 102 were in operation. The operating conditions of the plasma actuator 103 were such that ozone of 39 μg/min was generated when only the plasma actuator 103 was operated. Further, the operating conditions of the ultraviolet lamp 102 were such that the illuminance was 1370 $\mu W/cm^2$ when only the ultraviolet lamp 102 was operated. As a result, the amount of ozone generated when both the plasma actuator 103 and the ultraviolet lamp 102 were in operation was 8 μg/min. The decrease of 31 μg/min from 39 μg/min is considered to be the amount of ozone converted to active oxygen.

2-1. Treatment (Hydrophilization) Test

A polypropylene resin test piece (manufactured by TP Giken Co., Ltd.) was cut into a square with a length of 15 mm and a width of 15 mm to prepare the object 104 to be treated. The object to be treated was arranged in the opening 106 of the active oxygen supply device 101 prepared in Section 1 hereinabove so that the distance 405 in FIG. 4 was 3 mm. Next, a voltage having a sine waveform with an amplitude of 2.4 kV and a frequency of 80 kHz was applied to the plasma actuator, and ultraviolet light was emitted for 1 h to perform surface treatment of the object to be treated (treatment time: 1 h). Thereafter, the water contact angle of the surface of the polypropylene resin plate treated with the induced flow was measured and compared with the contact angle before the treatment. The contact angle was measured at 23° C. and 50% RH using an automatic contact angle meter (trade name: DMo-602, manufactured by Kyowa Interface Science Co., Ltd.) as a measuring instrument, a droplet of 0.5 μL of water was used, the angle was measured 500 ms after dropping, and the value obtained by averaging 5 points was adopted. The contact angle of the surface of the polypropylene resin plate before the treatment was 102°.

2-2. Treatment (Sterilization) Test (1) Preparation of Sample for Sterilization Test Three samples were prepared by the following method for use in the verification test of sterilization performance.

A stamp medium (trade name: PETAN CHECK 25 PT1025 manufactured by Eiken Chemical Co., Ltd.) was pressed for 10 sec under a pressure of 25 $g/cm^2$ against a door knob that had not been wiped with water, alcohol, etc. for a week in a location where an unspecified number of people entered and exited, and then the stamp medium was allowed to stand for 12 h in an environment at a temperature of 37° C. A colony grown in the stamp medium was collected using a sterile cotton swab and dispersed in distilled water to prepare a bacterial solution. A new stamp medium (PETAN CHECK 25 PT1025 manufactured by Eiken Chemical Co., Ltd.) was smeared with 0.1 ml of a diluted bacterial solution obtained by diluting this bacterial solution 10-fold with distilled water, and was allowed to stand for 12 h in an environment at a temperature of 37° C. As a result, growth of bacteria of 200 CFU/ml to 300 CFU/ml was observed. Then, 0.1 ml of the diluted bacterial solution was smeared on the entire surface of a glass plate (15 mm long, 15 mm wide, 2 mm thick) that had been cleaned with alcohol having a concentration of 70%. After that, the glass plate was placed in an environment at a temperature of 37° C. for 1 h to remove moisture. Thus, a total of three samples for sterilization tests were prepared.

(2) Sterilization Test

Figure 4:
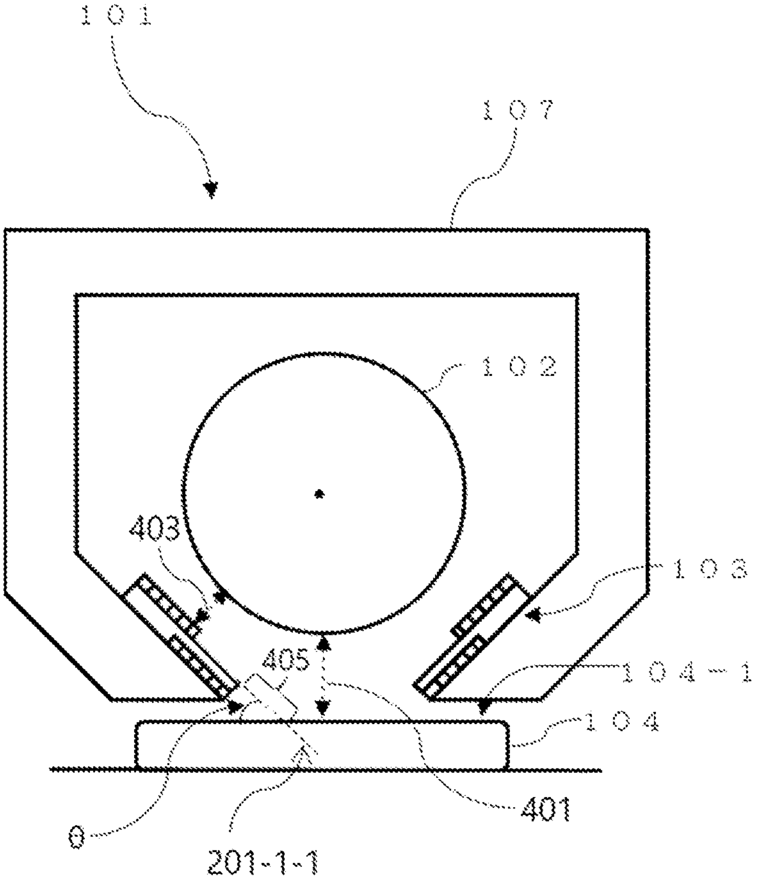
FIG. 4 is a dimensional explanatory diagram of an active oxygen supply device according to one embodiment of the present disclosure.

The active oxygen supply device 101 was arranged on the surface to be treated of each sample so that the distance 405 in FIG. 4 was 3 mm. Further, the center position in the width direction of the sample 104 (left-right direction in FIG. 4) was aligned with the center position in the width direction of the opening 106 and also aligned with the center position in the depth direction of the sample 104 (the depth direction of the paper surface in FIG. 4) and the center position in the depth direction of the opening 106. Next, a voltage having a sine waveform with an amplitude of 2.4 kV and a frequency of 80 kHz was applied to the plasma actuator 103, the ultraviolet lamp was turned on so that the illuminance on the surface of the glass plate 201 of the plasma actuator 103 facing the ultraviolet lamp was 1370 $\mu W/cm^2$, the induced flow and the surface to be treated were irradiated with ultraviolet light for 10 sec, the induced flow including active oxygen was caused to flow out from the opening 106, and the surface 104-1 to be treated was treated (treatment time: 10 sec). Next, a stamp medium (trade name: PETAN CHECK 25 PT1025 manufactured by Eiken Chemical Co., Ltd.) was pressed for 10 sec under a pressure of 25 $g/cm^2$ against the surface to be treated of the sample, and then the stamp medium was allowed to stand for 12 h in an environment at a temperature of 37° C. The number of surviving bacteria was calculated from the number of colonies grown on the medium. The average value of the number of surviving bacteria obtained from each sample was multiplied by 10 and used as the number of colonies in the sterilization test according to the present example. Based on the number of colonies obtained, the sterilization performance was evaluated according to the following criteria (Ten Cate determination display method).

−: No growth

±: Number of colonies <10

+: Number of colonies 10 to 29

++: Number of colonies 30 to 100

+++: Number of colonies >100

++++: Countless colonies 2-3. Treatment (Bleaching) Test (1) Preparation of Samples for Bleaching Test Chili sauce (trade name: PEPPER SAUCE, manufactured by Tabasco Co.) was filtered through a long-fiber nonwoven fabric (trade name: BEMCOT M-3II, manufactured by Asahi Kasei Corporation) to remove solids. A paper wiper (trade name: KIMWIPE S-200, manufactured by Nippon Paper Crecia Co., Ltd.) was immersed in the obtained liquid for 10 min. Subsequently, the paper wiper was taken out and washed with water. Washing with water was repeated until the washing liquid was no longer visually colored. Thereafter, drying was performed. Then, three samples having a length of 15 mm and a width of 15 mm were cut out from the paper wiper dyed red with the chili sauce.

(2) Bleaching Test

The active oxygen supply device 101 was arranged on the treatment surface of the obtained sample for bleaching test so that the distance 405 in FIG. 4 was 3 mm. The center position in the width direction of the sample 104 was aligned with the center position in the width direction of the opening 106 and also aligned with the center position in the depth direction of the sample 104 and the center position in the longitudinal direction of the opening 106. Next, a voltage having a sine waveform with an amplitude of 2.4 kV and a frequency of 80 kHz was applied to the plasma actuator 103, the ultraviolet lamp was turned on so that the illuminance on the surface of the glass plate 201 of the plasma actuator 103 facing the ultraviolet lamp was 1370 $\mu W/cm^2$, the induced flow and the surface to be treated was irradiated with ultraviolet light for 10 min, and the induced flow including active oxygen was supplied to a part of the surface 104-1 to be treated (treatment time: 10 min). Next, the active oxygen supply device 101 was removed from the surface to be treated, and the degree of decolorization was visually observed in comparison with the sample before the treatment and evaluated according to the following criteria.

A: Completely bleached.

B: The red color of the chili sauce remained slightly.

C: The red color of the chili sauce remained somewhat.

D: There was no difference in color from the portion where active oxygen was not supplied.

2-4. Treatment (Deodorization) Test (1) Preparation of Sample for Deodorization Test A paper wiper (KIMWIPE S-200, manufactured by Nippon Paper Crecia Co., Ltd.) was immersed in Fabric Mist (trade name: Fabric Mist-Linen, manufactured by SABON Co.) for 10 min, then taken out and allowed to dry naturally for 6 h. Then, the paper wiper was cut into a size of 10 mm long and 10 mm wide to obtain a sample for deodorization test.

(2) Deodorization Test

The active oxygen supply device 101 was arranged on the surface to be treated of each sample so that the distance 405 in FIG. 4 was 3 mm. The center position in the width direction of the sample was aligned with the center position in the width direction of the opening and also aligned with the center position in the depth direction of the sample and the center position in the longitudinal direction of the opening. Next, a voltage having a sine waveform with an amplitude of 2.4 kV and a frequency of 80 kHz was applied to the plasma actuator, the ultraviolet lamp was turned on so that the illuminance on the surface of the glass plate 201 of the plasma actuator 103 facing the ultraviolet lamp was 1370 $\mu W/cm^2$, the induced flow and the surface to be treated were irradiated with ultraviolet light for 10 sec, and the induced flow including active oxygen was supplied to a part of the surface to be treated (treatment time: 10 sec). Next, the active oxygen supply device was removed from the surface to be treated. The odor remaining in the treated sample was evaluated according to the following strength criteria in comparison with the sample that was not treated with active oxygen. The evaluation was performed by 5 subjects, and strength criteria selected by at least 3 subjects were adopted.

A: Odorless.

B: An odor that can barely be detected (detection threshold).

C: A weak odor that can be recognized as the odor of Fabric Mist (cognitive threshold).

D: No difference from untreated sample.

Example 2

An active oxygen supply device was produced and evaluated in the same manner as in Example 1, except that the voltage of the ultraviolet lamp 102 of Example 1 was lowered from 24 V to 12 V and the illuminance was lowered.

Examples 3 to 6

An active oxygen supply device was produced and evaluated in the same manner as in Example 1, except that the wavelength of the ultraviolet light source and the thickness and material of the dielectric of the plasma actuator were changed as shown in Table 1. In Example 6, an ultraviolet LED (peak wavelength: 280 nm) was used as an ultraviolet light source.

Comparative Examples 1 to 3

The conditions for Comparative Examples 1 to 3 were the same as those for Example 1, except that the following changes were made.

Comparative Example 1: No voltage was applied to the plasma actuator, and no ultraviolet light irradiation was performed.

Comparative Example 2: Voltage was applied to the plasma actuator, and no ultraviolet light irradiation was performed.

Comparative Example 3: No voltage was applied to the plasma actuator, and ultraviolet light irradiation was performed.

Example 7

Figure 5:
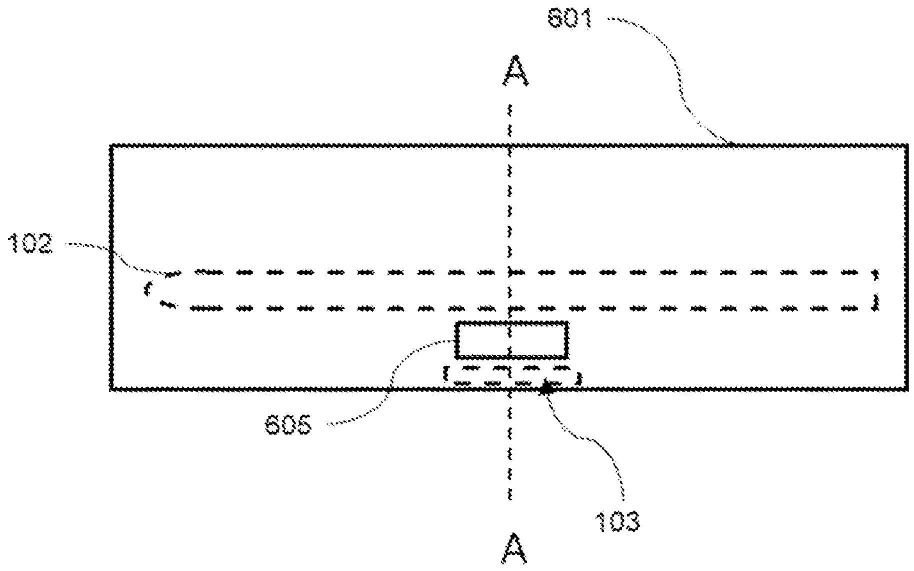
FIG. 5 is a plan view of the active oxygen supply device according to another embodiment of the present disclosure.

1. Production of Device for Treatment with Active Oxygen and Evaluation of Characteristics First, the housing 601 of the active oxygen supply device 600 shown in FIG. 6 was prepared. FIG. 5 is a plan view of the active oxygen supply device shown in FIG. 6 as viewed from the side of the housing 601 having the opening 605. The size of the housing was 20 mm in height, 150 mm in depth, and 20 mm in width when placed with the opening 605 facing vertically downward. The opening 605 had a width of 7 mm and a length of 15 mm. The opening 605 was provided so that the longitudinal direction thereof coincided with the depth direction of the housing, as shown in FIG. 5.

Figure 6:
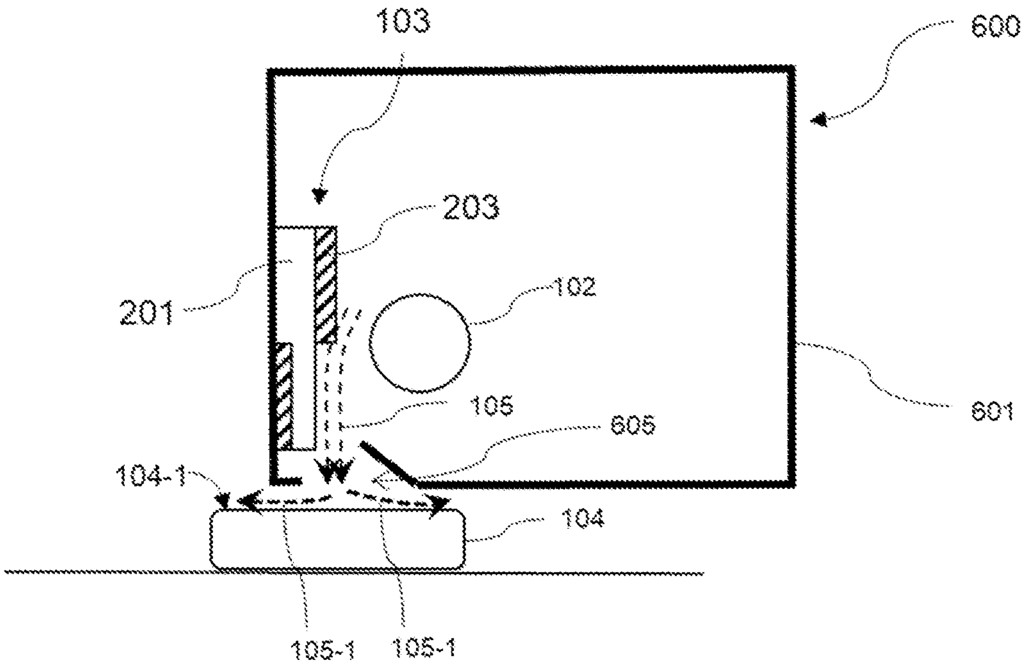
FIG. 6 is a cross-sectional view taken along line AA in FIG. 5.
Figure 7:
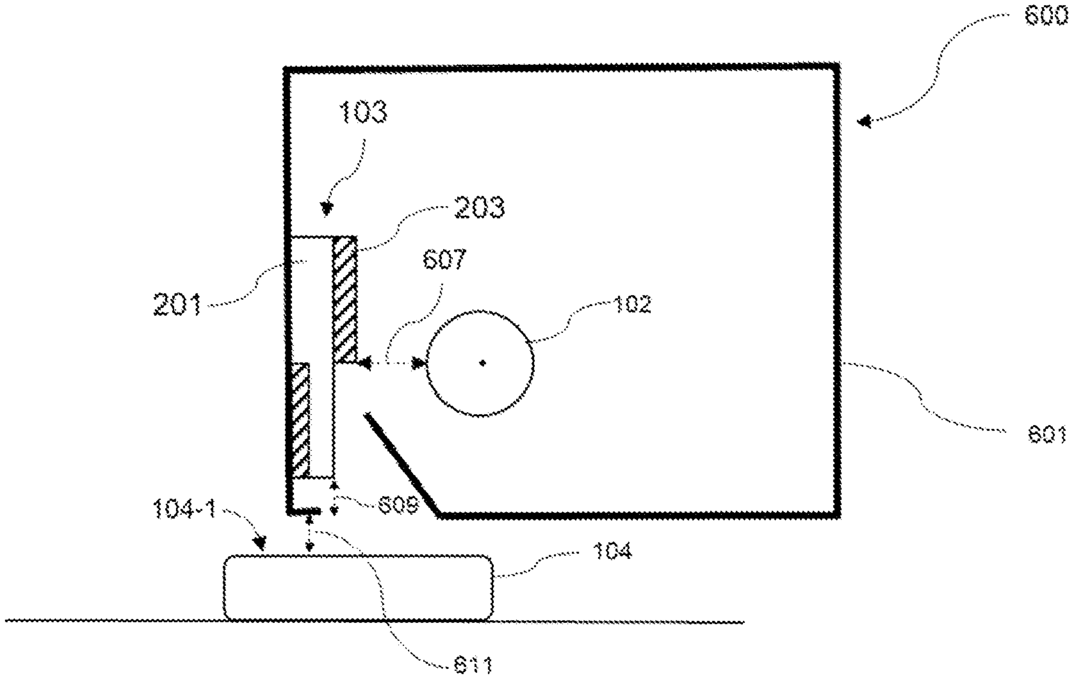
FIG. 7 is a schematic explanatory diagram of a treatment method using an active oxygen supply device according to another embodiment of the present disclosure.

Further, the plasma actuator 103 was produced in the same manner as in Example 1. The plasma actuator 103 was then fixed to the inner wall of the housing 601 as shown in FIG. 6. Specifically, one end of the first electrode 203 of the plasma actuator 103 was at a position horizontally aligned with the center of the ultraviolet light source 102 and was fixed so that the induced flow 105 from the plasma actuator 103 flowed out from the opening 605. Here, the distance (reference numeral 607 in FIG. 7) between the surface of the plasma actuator 103 facing the ultraviolet light source and the ultraviolet light source 102 was set to 2 mm, and the distance (reference numeral 609 in FIG. 7) between the lower end of the plasma actuator 103 and the lower end (outer side of the housing) of the opening 605 was set to 1 mm. As the ultraviolet light source 102, a cold-cathode ultraviolet lamp (trade name: UW/9F89/9, manufactured by Stanley Electric Co., Ltd., peak wavelength=254 nm) was used in the same manner as in Example 1.

For the active oxygen supply device 600 thus obtained, an illuminometer (trade name: Spectral Irradiance Meter USR-45D, manufactured by Ushio Inc.) was placed on the surface of the glass plate 201 of the plasma actuator 103 facing the ultraviolet lamp and the illuminance of ultraviolet light was measured. From the integrated value of the spectrum, the illuminance was 1370 μW/cm$^2$. Also, the illuminance of ultraviolet light when the illuminometer was placed in contact with the opening 605 was 0.3 μW/cm$^2$. From this, it was confirmed that there was substantially no leakage of ultraviolet light from the opening.

Next, a voltage having a sine waveform with an amplitude of 2.4 kV and a frequency of 80 kHz was applied between both electrodes of the plasma actuator 103 without turning on the power of the ultraviolet lamp so as to avoid the effect of the decomposition of ozone by ultraviolet light. After 5 min, 50 ml of the induced flow flowing out of the opening was sampled. The sampled gas was sucked into an ozone detection tube (trade name: 182SB, manufactured by Komyo Rikagaku Kogyo K.K.), and the concentration of ozone contained in the induced flow from the plasma actuator was measured to be 70 ppm (read value×2).

Next, a voltage having a sine waveform with an amplitude of 2.4 kV and a frequency of 80 kHz was applied between both electrodes of the plasma actuator, and the ultraviolet lamp was turned on so that the illuminance on the surface of the glass plate 201 of the plasma actuator 103 facing the ultraviolet lamp was 1370 μW/cm$^2$. Then, the ozone concentration in the induced flow flowing out from the opening at this time was measured in the same manner as described above. The result was 18 ppm. Based on these results, it is considered that this induced flow includes active oxygen generated by decomposing 52 ppm of ozone by ultraviolet light.

2. Treatment Tests

Using the active oxygen supply device prepared in Section 1 hereinabove, treatment tests were conducted in the same manner as the treatment (surface modification, sterilization, deodorization, bleaching) tests described in Example 1.

2-1. Surface Modification (Hydrophilization Treatment) Test

The active oxygen supply device according to the present embodiment was arranged on the surface to be treated of each sample so that the distance (reference numeral 611 in FIG. 7) between the outer surface of the housing having the opening and the surface to be treated was 2 mm. At this time, the center position in the width direction of the sample (left-right direction in FIG. 7) was aligned with the center position in the width direction of the opening and also aligned with the center position in the depth direction of the sample (depth direction in FIG. 7) and the center position in the longitudinal direction of the opening. Other than that, the hydrophilization treatment test was conducted in the same manner as the hydrophilization treatment test described in Example 1.

2-2. Sterilization Test

The active oxygen supply device according to the present embodiment was arranged on the surface to be treated of each sample so that the distance (reference numeral 611 in FIG. 7) between the outer surface of the housing having the opening and the surface to be treated was 2 mm. At this time, the center position in the width direction of the sample (left-right direction in FIG. 7) was aligned with the center position in the width direction of the opening and also aligned with the center position in the depth direction of the sample (depth direction of the paper surface in FIG. 7) and the center position in the longitudinal direction of the opening. Furthermore, the irradiation time of the induced flow with ultraviolet light was set to 30 sec (treatment time 30 sec). Other than that, the sterilization test was performed in the same manner as the sterilization test described in Example 1.

2-3. Bleaching Test

The active oxygen supply device was arranged on each sample so that the distance (reference numeral 611 in FIG. 7) between the outer surface of the housing having the opening and the surface to be treated was 2 mm, and the bleaching test was conducted in the same manner as the bleaching test described in Example 1, except that the irradiation time of the induced flow with the ultraviolet light was 20 min (treatment time 20 min).

2-4. Deodorization Test

The active oxygen supply device was arranged on the surface to be treated of each sample so that the distance between the lower end of the opening thereof and the surface to be treated was 2 mm. At this time, the center position in the width direction of the sample (left-right direction in FIG. 7) was aligned with the center position in the width direction of the opening and also aligned with the center position in the depth direction of the sample (the depth direction of the paper surface in FIG. 7) and the center position in the longitudinal direction of the opening. Furthermore, the irradiation time of the induced flow with ultraviolet light with respect to was set to 20 sec (treatment time 20 sec). Other than that, the deodorization test was conducted in the same manner as the deodorization test described in Example 1.

TABLE 1

| | UV peak wavelength (nm) | Thickness of dielectric (μm) | Dielectric material | Ozone concentration (μg/min) | UV illuminance (μW/cm$^2$) | Contact angle (°) | Sterilization performance determination (number of colonies) | Deodorization test | Bleaching test |
|---|---|---|---|---|---|---|---|---|---|
| Example 1 | 254 | 150 | Glass | 39 | 1370 | 67 | −(0) | A | A |
| Example 2 | 254 | 150 | Glass | 39 | 1070 | 71 | −(0) | A | A |
| Example 3 | 254 | 200 | Glass | 34 | 1370 | 69 | −(0) | A | A |
| Example 4 | 254 | 50 | Glass | 46 | 1370 | 66 | −(0) | A | A |
| Example 5 | 254 | 150 | Polyimide | 38 | 1370 | 67 | −(0) | A | A |
| Example 6 | 280 | 150 | Glass | 39 | 1370 | 70 | ±(9) | B | B |
| Example 7 | 254 | 150 | Glass | 40 | 1370 | 78 | −(0) | A | A |
| Comparative Example 1 | 254 | 150 | Glass | 0 | 0 | 102 | +++ | D | D |
| Comparative Example 2 | 254 | 150 | Glass | 39 | 0 | 90 | ++(41) | C | C |

TABLE 1-continued

| | UV peak wavelength (nm) | Thickness of dielectric (μm) | Dielectric material | Ozone concentration (μg/min) | UV illuminance (μW/cm$^2$) | Contact angle (°) | Sterilization performance determination (number of colonies) | Deodorization test | Bleaching test |
|---|---|---|---|---|---|---|---|---|---|
| Comparative Example 3 | 254 | 150 | Glass | 0 | 1370 | 102 | ++(32) | D | D |

In the table, PA represents the plasma actuator, and UV represents ultraviolet rays. Further, the ozone concentration indicates the ozone concentration when the ultraviolet light source is not turned on.

Device conditions of the active oxygen supply devices of Examples 1 to 7 and Comparative Examples 1 to 3, ozone concentration when only the plasma actuator is operated, illuminance of ultraviolet light when only the UV cold cathode tube is operated, decrease in contact angle, and the evaluation results of the sterilization/deodorization/bleaching treatments are shown in Table 1.

A decrease in the contact angle did not occur due to ultraviolet light as shown in Comparative Example 3. Further, when ozone was generated as in Comparative Example 2, the contact angle decreased. Furthermore, when both ozone generation and ultraviolet irradiation were performed, the contact angle further decreased due to the high reactivity of active oxygen.

In Comparative Example 1, neither the plasma actuator nor the active oxygen was operated, so there were no effects of sterilization, deodorization and bleaching by ultraviolet light, ozone, and active oxygen. In Comparative Example 2, the effects of sterilization, deodorization and bleaching caused by ozone were observed to some extent, but not as high as in Examples 1 to 7. In Comparative Example 3, the effect of sterilization by ultraviolet light was observed to some extent, but the effects of deodorization and bleaching were not observed.

Example 8

Using the active oxygen supply device produced in Example 1, an *Escherichia coli* sterilization test was carried out according to the following procedure. All instruments used in this sterilization test were sterilized with high-pressure steam using an autoclave. In addition, this sterilization test was conducted in a clean bench.

First, *Escherichia coli* (trade name "KWIK-STIK (*Escherichia coli* ATCC8739), manufactured by Microbiologics)" was placed in an Erlenmeyer flask containing LB medium (distilled water was added to 2 g of tryptone, 1 g of yeast extract, and 1 g of sodium chloride to make 200 ml) and cultured with shaking at 80 rpm at a temperature of 37° C. for 48 h. The bacterial suspension of *Escherichia coli* after culturing was $9.2\times10^9$ (CFU/ml).

Using a micropipette, 0.010 ml of the cultured bacterial suspension was dropped onto a slide glass (Matsunami glass, model number: S2441) having a length of 3 cm, a width of 1 cm, and a thickness of 1 mm, and the bacterial suspension was coated on the entire surface on one side of the slide glass with the tip of the micropipette to prepare sample No. 8-1. Samples Nos. 8-2 and 8-3 were produced in a similar manner.

Next, sample No. 8-1 was immersed for 1 h in a test tube containing 10 ml of buffer solution (trade name "Gibco PBS", Thermo Fisher Scientific Inc.). To prevent the bacterial suspension on the slide glass from drying, the time from dropping the bacterial suspension onto the slide glass to immersing it in the buffer solution was set to 60 sec.

Next, 1 ml of the buffer solution into which sample No. 8-1 was immersed (hereinafter referred to as "1/1 solution") was placed in a test tube containing 9 ml of buffer solution to prepare a diluted solution (hereinafter referred to as "1/10 diluted solution"). A 1/100 diluted solution, a 1/1000 diluted solution, and a 1/10,000 diluted solution were prepared in the same manner, except that the dilution ratio with the buffer solution was changed.

Next, 0.050 ml was sampled from the 1/1 solution and smeared on a stamp medium (PETAN CHECK 25, PT1025, manufactured by Eiken Chemical Co., Ltd.). This operation was repeated to prepare two stamp media smeared with the 1/1 solution. The two stamp media were placed in a thermostat (trade name: IS600; manufactured by Yamato Scientific Co., Ltd.) and cultured at a temperature of 37° C. for 24 h. The number of colonies generated on the two stamped media was counted, and the average value was calculated.

For the 1/10 diluted solution, 1/100 diluted solution, 1/1000 diluted solution and 1/10,000 diluted solution, two smeared stamp media were prepared and cultured for each diluted solution in the same manner as above. Then, the number of colonies generated in each stamp medium for each diluted solution was counted, and the average value was calculated. Table 2 shows the results.

TABLE 2

| | Sample No. 8-1 (blank) |
|---|---|
| 1/1 solution | >300 |
| 1/10 diluted solution | >300 |
| 1/100 diluted solution | >300 |
| 1/1000 diluted solution | 179 |
| 1/10000 diluted solution | 21 |

From the results shown in Table 2 above, it was found that the number of colonies when culturing the 1/10,000 diluted solution was 21 and therefore, the number of bacteria present in 0.050 ml of the 1/1 solution related to sample No. 8-1 was $21\times10^4$=210,000 (CFU).

Next, the following operations were performed with respect to samples Nos. 8-2 and 8-3.

A recess having a length of 3.5 cm long, a width of 1.5 cm, and a depth of 2 mm was provided in the center of a plastic flat plate having a length of 30 cm, a width of 30 cm, and a thickness of 5 mm, and the slide glass was placed into the recess so that the surface of the slide glass of each sample on the side opposite that coated with the bacterial solution was in contact with the bottom surface of the recess. Then, the active oxygen supply device was placed on the upper surface of the plastic plate so that the center in the longitudinal direction of the opening of the active oxygen supply device coincided with the center in the longitudinal direction of the recess and also so that the center in the width direction of the opening of the active oxygen supply device coincided with the center in the lateral direction of the recess. Since the depth of the recess was 2 mm and the thickness of the slide glass was 1 mm, the surface of each sample to which the bacterial solution had adhered did not come into direct contact with the opening of the active oxygen supply device.

Next, the active oxygen supply device was actuated, and the surface of the slide glass coated with the bacterial solution was treated with an induced flow including active oxygen. The treatment time was 2 sec for sample No. 8-2 and 10 sec for sample No. 8-3. In addition, the time from dropping the bacterial solution onto the slide glass to immersing in the buffer solution was set to 60 sec so that the bacterial solution on the slide glass did not dry in the treatment process using the active oxygen supply device.

The treated samples Nos. 8-2 and 8-3 were immersed for 1 h in a test tube containing 10 ml of buffer solution (trade name "Gibco PBS", Thermo Fisher Scientific Inc.). Next, 1 ml of the buffer solution into which each sample was immersed (hereinafter referred to as "1/1 solution") was placed in a test tube containing 9 ml of buffer solution to prepare a diluted solution (1/10 diluted solution). A 1/100 diluted solution, a 1/1000 diluted solution, and a 1/10,000 diluted solution were prepared in the same manner, except that the dilution ratio with the buffer solution was changed.

Next, 0.050 ml was sampled from the 1/1 solution of each sample and smeared on a stamp medium (PETAN CHECK 25, PT1025, manufactured by Eiken Chemical Co., Ltd.). This operation was repeated to prepare two stamp media smeared with the 1/1 solution for each sample. A total of four stamp media were placed in a thermostat (trade name: IS600; manufactured by Yamato Scientific Co., Ltd.) and cultured at a temperature of 37° C. for 24 h. The number of colonies generated on the two stamped media was counted, and the average value was calculated.

For the 1/10 diluted solution, 1/100 diluted solution, 1/1000 diluted solution and 1/10,000 diluted solution, two smeared stamp media were prepared and cultured for each diluted solution in the same manner as described above. Then, the number of colonies generated in each stamp medium for each diluted solution of each sample was counted, and the average value was calculated. Table 3 shows the results.

TABLE 3

| | Sample No. 8-2 (treatment time 2 sec) | Sample No. 8-3 (treatment time 10 sec) |
|---|---|---|
| 1/1 solution | 0 | 0 |
| 1/10 diluted solution | 0 | 0 |
| 1/100 diluted solution | 0 | 0 |
| 1/1000 diluted solution | 0 | 0 |
| 1/10000 diluted solution | 0 | 0 |

As mentioned above, the number of bacteria in 0.050 ml of the 1/1 solution related to sample No. 8-1 was 210,000 (CFU). The number of bacteria in the 1/1 solutions related to samples Nos. 8-2 and 8-3 after the sterilization treatment was 0 (CFU). From this, it was understood that the active oxygen supply device according to the present embodiment can sterilize *Escherichia coli* with a high efficiency of 99.999% ((210,000−1)/210,000×100) or more even when the treatment time is 2 sec.

Comparative Example 4

Samples Nos. C4-1 and C4-2 were prepared in the same manner as in the method for preparing sample No. 8-1 described in Example 8. These samples Nos. C4-1 and C4-2 were treated in the same manner as in Example 8, except that no voltage was applied to the plasma actuator of the active oxygen supply device. The treatment time was 2 sec for sample No. C4-1 and 10 sec for sample No. C4-2. For treated samples Nos. C4-1 and C4-2, immersion in a buffer solution was performed in the same manner as for sample No. 8-1 of Example 8. Next, a smeared stamp medium was prepared and cultured with respect to the 1/1 solution of each sample. The number of colonies generated in each stamp medium related to the 1/1 solution of each sample was counted, and the average value was calculated. Table 4 shows the results.

TABLE 4

| | Sample No. C4-1 (treatment time 2 sec) | Sample No. C4-2 (treatment time 10 sec) |
|---|---|---|
| 1/1 solution | 52 | 0 |

From the results of culturing the 1/1 diluted solution of sample No. C4-1 after the treatment, it was found that the number of bacteria present in 0.050 ml of the 1/1 solution related to sample No. C4-1 after the treatment was 52 (CFU). Meanwhile, the number of bacteria present in 0.050 ml of the 1/1 solution related to sample No. C4-2 was 0 (CFU). Therefore, in the present comparative example, the sterilization rate of *Escherichia coli* when the treatment time was 2 sec was 99.98% (=(210,000−52)/210,000×100).

In Example 8, as described above, the sterilization rate was 99.999% or more when the treatment time was 2 sec. As a result, it was confirmed that the sterilization efficiency of the treatment using only ultraviolet light was inferior to that of the treatment using both ultraviolet light and active oxygen.

Comparative Example 5

Samples Nos. C5-1 and C5-2 were prepared in the same manner as in the method for preparing sample No. 8-1 described in Example 8. These samples Nos. C5-1 and C5-2 were treated in the same manner as in Example 8, except that the ultraviolet lamp of the active oxygen supply device was not turned on. Therefore, samples Nos. C5-1 and C5-2 were treated with ozone in the induced flow. The treatment time was 2 sec for sample No. C5-1 and 10 sec for sample No. C5-2. For treated samples Nos. C5-1 and C5-2, immersion and dilution in a buffer solution were performed in the same manner as for sample No. 8-1 in Example 8. Next, two smeared stamp media were prepared and cultured with respect to each of the 1/1 solution, 1/10 diluted solution, 1/100 diluted solution, 1/1000 diluted solution and 1/10,000 diluted solution related to each of sample in the same manner as for sample No. 8-1 of Example 8. Then, the number of colonies generated in each stamp medium related to the 1/1 solution and each diluted solution for each sample was counted, and the average value was calculated. Table 5 shows the results.

TABLE 5

| | Sample No. C5-1 (treatment time 2 sec) | Sample No. C5-2 (treatment time 10 sec) |
|---|---|---|
| 1/1 solution | >300 | >300 |
| 1/10 diluted solution | >300 | >300 |
| 1/100 diluted solution | >300 | >300 |

TABLE 5-continued

| | Sample No. C5-1 (treatment time 2 sec) | Sample No. C5-2 (treatment time 10 sec) |
|---|---|---|
| 1/1000 diluted solution | 185 | 93 |
| 1/10000 diluted solution | 19 | 8 |

Among the above results, from the results of culturing the 1/10,000 diluted solution of sample No. C5-1 after the treatment, it was found that the number of bacteria present in 0.050 ml of the 1/1 solution related to sample No. C5-1 after the treatment was $19\times10^4$=190,000 (CFU). Therefore, in the test example using sample No. C5-1, the sterilization rate of *Escherichia coli* was 9.5% (=(210,000−190,000)/210,000×100).

Further, from the results of culturing the 1/10,000 diluted solution of sample No. C5-2, it was found that the number of bacteria present in 0.050 ml of the 1/1 solution related to sample No. C5-2 after the treatment was $8\times10^4$=80,000 (CFU). Therefore, in the test example using sample No. C5-2, the sterilization rate of *Escherichia coli* was 61.9% (=(210,000−80,000)/210,000×100).

In Example 8, the sterilization rate was 99.999% or more even when the treatment time was 2 sec. As a result, it was confirmed that the sterilization efficiency of the treatment using only ozone was inferior to that of the treatment using both ultraviolet light and active oxygen.

Example 9

The slide glass used in the preparation of sample No. 8-1 in Example 8 was changed to qualitative filter paper (product number: No. 5C, manufactured by Advantec Co., Ltd.) having a length of 3 cm and a width of 1 cm. In addition, the bacterial solution was only dropped onto one side of the filter paper. Other than these, sample No. 9-1 was prepared in the same manner as sample No. 8-1.

Next, the following operations were performed with respect to sample No. 9-1.

A recess having a length of 3.5 cm long, a width of 1.5 cm, and a depth of 2 mm was provided in the center of a plastic flat plate having a length of 30 cm, a width of 30 cm, and a thickness of 5 mm. A filter paper having a length of 3.5 cm and a width of 1.5 cm was laid in the recess. Sample No. 9-1 was arranged on the filter paper so that the bacterial solution dropping surface thereof faced the filter paper laid on the bottom of the recess. Then, the active oxygen supply device was placed on the upper surface of the plastic plate so that the center in the longitudinal direction of the opening of the active oxygen supply device coincided with the center in the longitudinal direction of the recess and also so that the center in the width direction of the opening of the active oxygen supply device coincided with the center in the lateral direction of the recess. Since the depth of the recess was 2 mm and the thickness of the filter paper was 1 mm or less, the surface of each sample to which the bacterial solution had adhered did not come into direct contact with the opening of the active oxygen supply device. Next, the active oxygen supply device was actuated, and the surface of the bacterial solution dropping surface of the filter paper was treated with an induced flow including active oxygen. The treatment time was 10 sec. In addition, the time from dropping the bacterial solution onto the filter paper to immersing in the buffer solution was set to 60 sec so that the filter paper onto which the bacterial solution had been dropped did not dry in the treatment process using the active oxygen supply device.

The treated sample No. 9-1 was immersed for 1 h in a test tube containing 10 ml of buffer solution (trade name "Gibco PBS", Thermo Fisher Scientific Inc.). Next, 1 ml of the buffer solution after the immersion (hereinafter referred to as "1/1 solution") was placed in a test tube containing 9 ml of buffer solution to prepare a diluted solution (1/10 diluted solution). A 1/100 diluted solution, a 1/1000 diluted solution, and a 1/10,000 diluted solution were prepared in the same manner, except that the dilution ratio with the buffer solution was changed.

Next, 0.050 ml was sampled from the 1/1 solution and smeared on a stamp medium (trade name: PETAN CHECK 25, PT1025, manufactured by Eiken Chemical Co., Ltd.). This operation was repeated to prepare two stamp media smeared with the 1/1 solution. A total of two stamp media were placed in a thermostat (trade name: IS600; manufactured by Yamato Scientific Co., Ltd.) and cultured at a temperature of 37° C. for 24 h. The number of colonies generated in each stamp medium related to the 1/1 solution was counted, and the average value was calculated.

For the 1/10 diluted solution, 1/100 diluted solution, 1/1000 diluted solution and 1/10,000 diluted solution, two smeared stamp media were prepared and cultured for each diluted solution in the same manner as above. Then, the number of colonies generated in each stamp medium for each diluted solution was counted, and the average value was calculated.

Comparative Example 6

Sample No. C9 was prepared in the same manner as sample No. 9-1.

This sample No. C9 was treated in the same manner as in Example 9, except that no voltage was applied to the plasma actuator of the active oxygen supply device. That is, sample No. C9 was irradiated only with UV light. The treatment time was 10 sec. For treated sample No. C9, immersion in a buffer solution was performed in the same manner as for sample No. 9 of Example 9. A 1/1 solution and 1/10 to 1/10,000 diluted solutions were prepared in the same manner as in Example 9 except that the obtained buffer solution after immersion was used. Stamp media were prepared and cultured in the same manner as in Example 9, except that the prepared 1/1 solution and 1/10 to 1/10,000 diluted solutions were used, the number of colonies generated in each stamp medium related to the 1/1 solution and each diluted solution was counted, and the average value was calculated.

Reference Example 1

Sample No. R1 was prepared in the same manner as sample No. 9-1.

Untreated sample No. R1 was immersed for 1 h in a test tube containing 10 ml of buffer solution (trade name "Gibco PBS", Thermo Fisher Scientific Inc.). Next, 1 ml of the buffer solution after the immersion (hereinafter referred to as "1/1 solution") was placed in a test tube containing 9 ml of buffer solution to prepare a diluted solution (1/10 diluted solution). A 1/100 diluted solution, a 1/1000 diluted solution, and a 1/10,000 diluted solution were prepared in the same manner, except that the dilution ratio with the buffer solution was changed.

Next, 0.050 ml was sampled from the 1/1 solution and smeared on a stamp medium (PETAN CHECK 25, PT1025, manufactured by Eiken Chemical Co., Ltd.). This operation was repeated to prepare two stamp media smeared with the 1/1 solution. A total of two stamp media were placed in a thermostat (trade name: IS600; manufactured by Yamato Scientific Co., Ltd.) and cultured at a temperature of 37° C. for 24 h. The number of colonies generated on each stamped medium related to the 1/1 solution of sample No. R1 was counted, and the average value was calculated.

For the 1/10 diluted solution, 1/100 diluted solution, 1/1000 diluted solution and 1/10,000 diluted solution, two smeared stamp media were prepared and cultured for each diluted solution in the same manner as described above. Then, the number of colonies generated in each stamp medium for each diluted solution was counted, and the average value was calculated.

Table 6 shows the results of Example 9, Comparative Example 6 and Reference Example 1.

TABLE 6

| | Example 9 (treatment time 10 sec) | Comparative Example 6 (treatment time 10 sec, only irradiation with UV) | Reference Example 1 (no treatment) |
|---|---|---|---|
| 1/1 solution | 0 | >300 | >300 |
| 1/10 diluted solution | 0 | 103 | >300 |
| 1/100 diluted solution | 0 | 10 | 54 |
| 1/1000 diluted solution | 0 | 2 | 5 |
| 1/10000 diluted solution | 0 | 0 | 0 |

From the results of culturing of the 1/1000 diluted solution of Reference Example 1, it was found that the number of bacteria present in 0.050 ml of the 1/1 solution of sample No. R1 was $5\times10^3$=5000 (CFU). Further, the number of bacteria in 0.050 ml of the 1/1 solution after the treatment in Example 9 was 0 (CFU). From this, it was found that the sterilization rate of *Escherichia coli* in Example 9 was 99.98% ((5000−1/5000)×100) or more. Meanwhile, from the results of culturing of the 1/1000 diluted solution of Comparative Example 6, it was found that the number of bacteria present in 0.050 ml of the 1/1 solution related to sample No. C6 after the treatment was $2\times10^3$=2000 (CFU). Therefore, it was found that the sterilization rate of *Escherichia coli* in Comparative Example 6 was 60% ((5000−2000)/5000)×100).

Here, sample No. 9-1 was treated with active oxygen on the surface opposite to the bacterial solution dropping surface of the filter paper related to sample No. 9-1. From the results of Example 9 and Comparative Example 6, it was understood that the sterilization treatment by actively supplying active oxygen to the object to be treated can more reliably sterilize not only *Escherichia coli* present on the surface of the filter paper but also *Escherichia coli* present inside the filter paper. In this respect, the sterilization method according to the present disclosure is superior to the sterilization method using only UV, which sterilizes only the surface irradiated with UV light.

While the present disclosure has been described with reference to exemplary embodiments, it is to be understood that the disclosure is not limited to the exemplary embodiments. The scope of the following claims is to be accorded the broadest interpretation so as to encompass all such modifications and equivalent structures and functions.

What is claimed is:

1. An active oxygen supply device comprising:
a housing, with an opening formed in the housing,
a plasma actuator in the housing, and
an ultraviolet light source in the housing,
wherein the plasma actuator comprises:
a dielectric substrate;
a first electrode provided on a first surface of the dielectric substrate; and
a second electrode provided on a second surface that is opposite to the first surface of the dielectric substrate,
wherein the first electrode and the second electrode are arranged with the dielectric substrate in-between and are obliquely arranged opposite to each other with parts of the first electrode and the second electrode being offset from each other,
wherein the plasma actuator generates an induced flow including ozone in a direction from an edge of the first electrode along an exposed portion of the dielectric substrate when a voltage is applied between the first electrode and the second electrode, with the exposed portion being not covered with the first electrode,
wherein the induced flow flows out of the housing from the opening, and
wherein the ultraviolet light source irradiates the induced flow with ultraviolet light and generates active oxygen in the induced flow, and
wherein a narrow angle 0 formed by a line extending from the edge of the first electrode of the plasma actuator in a direction along a portion of the dielectric substrate not covered by the first electrode and a horizontal plane when the opening of the active oxygen supply device is directed vertically downward is 0° to 90°.

2. The active oxygen supply device according to claim 1, wherein the ultraviolet light emitted from the ultraviolet light source has a peak wavelength of 220 nm to 310 nm.

3. The active oxygen supply device according to claim 1, wherein the ultraviolet light in the opening has an illuminance of 40 $\mu W/cm^2$ or more.

4. The active oxygen supply device according to claim 1, wherein the amount of ozone generated per unit time in the plasma actuator in a state where the induced flow is not irradiated with the ultraviolet light is 15 μg/min or more.

5. The active oxygen supply device according to claim 1, wherein a distance between the ultraviolet light source and the plasma generator is 10 mm or less.

6. The active oxygen supply device according to claim 1, wherein the ultraviolet light source irradiates an object to be treated placed outside the housing through the opening.

* * * * *